United States Patent [19]

Grassin et al.

[11] Patent Number: 5,578,335
[45] Date of Patent: Nov. 26, 1996

[54] PROCESS FOR THE PRODUCTION OF JUICES FROM FRUITS AND VEGETABLES

[75] Inventors: Catherine M. T. Grassin; Pierre C. L. Fauquembergue, both of Seclin, France

[73] Assignee: Gist-brocades, B.V., Delft, Netherlands

[21] Appl. No.: 78,261

[22] PCT Filed: Nov. 6, 1992

[86] PCT No.: PCT/EP92/02576

§ 371 Date: Aug. 12, 1993

§ 102(e) Date: Aug. 12, 1993

[87] PCT Pub. No.: WO93/09683

PCT Pub. Date: May 27, 1993

[30]  Foreign Application Priority Data

Nov. 14, 1991 [EP] European Pat. Off. .............. 91202971

[51] Int. Cl.⁶ ........................................................ A23L 2/02
[52] U.S. Cl. .................. 426/51; 426/49; 426/50; 426/52; 426/577; 426/599
[58] Field of Search .................................. 426/49, 50, 51, 426/52, 590, 599, 577, 615, 616

[56]  References Cited

U.S. PATENT DOCUMENTS

| | | |
|---|---|---|
| 4,200,694 | 4/1980 | Ishii et al. . |
| 4,374,865 | 2/1983 | Strobel .................................. 426/599 |
| 4,463,025 | 7/1984 | Strobel .................................. 426/599 |
| 4,569,853 | 2/1986 | Strobel .................................. 426/599 |

FOREIGN PATENT DOCUMENTS

| | | |
|---|---|---|
| 202620 | 9/1983 | German Dem. Rep. . |
| 2843351 | 4/1979 | Germany . |
| 3444086A1 | 6/1986 | Germany . |
| 246025 | 5/1987 | Germany . |
| 249919 | 9/1987 | Germany . |

OTHER PUBLICATIONS

Graham, H. D., "Food Colloids", 1977, The AVI Publishing Company, Inc., Westport, CT, pp. 425–428.
Friedrich et al., Production of pectolytic enzymes by Aspergillus niger: effect of inoculum size and potassium hexacynoferrate II–trihydrate, Applied microbiology and Biotechnology, (1990) 33(4) 377–381, abstract only.
Norz, K., "Theoretische Grundlagen und Verarbeitung in Geleefruchten", Zucker und Susswaren Wirtschaft 38:5–6 (1985).
Pilnik W. and A. Voragen, "The Biochemistry of Fruits and their Products", vol. 1, Chapter 3, p. 53, Acad. Press (1970).
Aspinall, G. and Fanous, "Structural Investigations on the Non–starchy Polysaccharides of Apples", Carbohydrate Polym. 4:193 (1984).
Walkinshaw, M. and S. Arnott, "Conformations and Interactions of Pectins", J. Mol. Biol. 153:1075 (1981).
Perring, A. et al., "The Distribution of Calcium in Apples with Senescent Breakdown", J. Sci. Food Agric. 36:1035 (1985).
Endo, A., "Studies on Pectolytic Enzymes of Moldes", Agric. Biol. Chem. 29(2):137 (1965).
Voragen, A. and W. Pilnik, "Pectin–Degrading Enzymes in Fruit and Vegetable Processing", Biocatalysis in Agricultural Biotechnology, ACS Symposium Series 389, Chapter 7, p. 93 (1989).
Voragen A. et al., "Non–enzymatic browning of oligogalacturonides in apple juice models", Z. Lebnsm. Forsch. 187:315–320 (1988).

*Primary Examiner*—Leslie Wong
*Attorney, Agent, or Firm*—Morrison & Foerster LLP

[57] ABSTRACT

The present invention discloses the application of a pectin esterase substantially free from depolymerase activity in the maceration of apple pulp. The use of purified pectin esterase leads to a low amount of pectin degradation products in the juice and to the conservation of protopectin in the apple pomace. Furthermore, the juice yield and the pressability are increased through the use of purified PE.

11 Claims, 10 Drawing Sheets

PROCESS FOR THE PRODUCTION OF JUICES FROM FRUITS AND VEGETABLES

FIELD OF THE INVENTION

The present invention relates to a process for the production of juices and pectin-containing pomace from fruits and vegetables. Specifically, the invention discloses the use of purified pectin esterase in the process of juice production.

BACKGROUND OF THE INVENTION

Juice production and the yield thereof from fruits and vegetables can be understood by looking at the different components involved in the process. The components important for the present invention are pectin, protopectin, calcium ions and pectinases.

Pectins are major constituents of the cell walls of edible parts of fruits and vegetables. The middle lamella which are situated between the cell walls are mainly built up from protopectin which is the insoluble form of pectin. Pectins are considered as intercellular adhesives and due to their colloid nature they also have an important function in the water-regulation of plants. Water-binding capacity is greatly increased by the amount of hydrophylic hydroxyl and carboxyl groups. The amount of pectin can be very high. For example, lemon peels are reported to contain pectin up to 30% of their dry weight, orange peels contain from 15–20% and apple peels about 10% (Norz, K., 1985. Zucker und S üsswaren Wirtschaft 38 5–6).

Pectins are composed of a rhamno-galacturonan backbone in which 1,4-linked α-D-galacturonan chains are interrupted at intervals by the insertion of 1,2-linked α-L-rhamnopyranosyl residues (Pilnik, W. and A. Voragen 1970. In 'The Biochemistry of fruits and their products', Vol. 1, Chapter 3, p.53. Acad. Press). Other sugars, such as D-galactose, L-arabinose and D-xylose, are present as side chains. A large part of the galacturonan residues is esterified with methyl groups at the C2 and C3 position. Apple pectin is methylated to a degree of about 90% (Aspinall, G. and Fanous, 1984. Carbohydrate Polym. 4 p. 193). Pectin exist in two forms, pectin and protopectin. Protopectin is pectin which is insoluble in water and strongly bound to the cell wall (Joslyn, M. 1962, Food Research Vol. 11, p.1–107. Acad. Press)

In fruit such as apples, during the maturation an increase of the soluble pectin content and a decrease of the non-soluble protopectin content can be observed. The release of apple pectin is due to a partial solubilization of the protopectin from the lamella. This solubilization or pectinolysis is due to the endogenous pectinases present in the fruit. As a result of this process the amount of pectin in the juice after pressing increases whereas the amount of protopectin left in the pomace decreases with storage time of the fruit.

Calcium ions are present in free form in the apple pulp or bound to the pectic acid in the form of calcium pectate which increases the firmness of the pulp. (Walkinshaw, M. and S. Arnott, 1981. J. Mol. Biol. 153 p.1075). After harvesting, and at least partially due to pectinolysis and dehydrating of the apples, the bound calcium is released and migrates into the apples. This release of calcium further increases protopectin solubilization (Perring, A. et al. 1985. J. Sci. Food Agric. 36 p. 1035). At the same time this process leads to a decrease of the pulp firmness.

Both the endogenous apple pectinases and the endogenous calcium have a major effect on the residual amount of protopectin in the pomace. The apple pomace contains a high amount of protopectin at the beginning of the season, which decreases due to the combined action of endogenous pectinase activities and calcium migration. This is the major reason why the pectin manufacturer prefers the use of pomace obtained early in the harvesting season in order to secure a high process yield.

Apple or citrus pectins are used in the preparation of food for their gelating capacity. Apple pectin is used for jelly or jam production since it gelifies under acidic conditions in the presence of sugar.

In the classical juice production process, apple juice is obtained after grinding and pressing which separates the liquid phase from the residual solids. In pectin-rich fruit such as apple, mechanical crushing gives an apple juice with a high viscosity which increases with the maturation time of the fruit. Furthermore, a substantial part of the juice remains in the pulp in the form of a gel. After prolonged storage of the apples it becomes more and more difficult to extract the juice from the pulp by pressing or other mechanical methods due to the increase in the amount of soluble pectin. Therefore, the apple juice yield decreases with time. The apple juice obtained after enzymatic maceration and pressing is depectinized with exogenous pectinases, clarified by fining agents or ultra-filtration, pasteurized and bottled or concentrated by evaporation under vacuum. The pomace which is a leftover of the apple juice preparation can subsequently be used for pectin extraction. In this process no maceration enzymes are employed.

In an improved juice production process the juice yield is substantially increased by adding exogenous pectinases to the apples before pressing (Endo A., 1965. Agric. Biol. Chem. 29(2) p. 137). The pectinase preparations most widely used for fruit maceration are capable of rapid degradation of highly esterified pectins (Voragen, A. and W. Pilnik 1989. In 'Biocatalysis in Agricultural Biotechnology', ACS Symposium series 389, chapter 7, p.93). The pectinase preparations generally consist of a mixture of activities. The activities in these mixture are dependent on the source from which they are obtained. Based on enzymatic activity the pectinases are classified in two groups: the saponifying enzymes (pectin methyl esterase PME and pectin acetyl esterase PAE) and the depolymerase enzymes which digest the polygalacturonic chains. The enzymes involved in the second group are a pectin lyase (PL) and polygalacturonases (PG) (exo or endo).

The use of these enzymes is dependent on the substrate, the degree of methylation and the molecular weight of the pectin. PE and PG or PL first act to solubilize the protopectin in pectin and subsequently hydrolyze the pectin from the cell wall, thereby at the same time releasing the juice contained inside the cell vacuola.

The increased pulp pressability and the increase in juice yield are due to the fact that degraded pectins have lost their capacity to bind water. The enzymatic treatment improves the juice yield of apples which are difficult to press and also from apples stored for longer periods of time.

Pectin hydrolysis stimulated by the addition of exogenous pectinases gives a rapid decrease in viscosity, an improvement of the pulp pressability, a disintegration of the jelly structure and a higher apple juice yield. However, the exogenous pectinases consisting of a mixture of enzymatic activities (such as PE, PG and PL) at the same time release and degrade the main part of the protopectin which is bound in the pomace. The pomace cannot be used economically anymore for the production of pectin. Furthermore, this stimulated enzymatic degradation of pectin gives rise to an increase in degradation products like uronic acid, or more generally, oligogalacturonides in the juice. These degradation products cause undesired non-enzymatic browning during storage (Voragen A. et al., 1988. Z.Lebensm. Forsch. 187 p.315–320).

Summarising, it can be concluded that in the classical juice preparation procedure the juice yield is relatively low, the juice is cloudy and the amount of pectin which can be extracted from the pomace is high. Introduction of pectinases lead to an increased juice yield, a lower protopectin content of the pomace and unwanted side-reactions giving rise to browning of the juice.

Clearly there is a need for an enzyme preparation which combines the advantages of an increase in apple juice yield and improved pressability with the absence of unwanted side-reactions of the enzymes and the lack of undesired hydrolysis of the protopectin which is present in the cell walls.

SUMMARY OF THE INVENTION

The present invention provides a process for the production of juices and pectin-containing pomace from fruits or vegetables which comprises the use of a substantially pure pectin esterase. Preferably, the pectin esterase is free from pectin depolymerase activity, more specifically the pectin esterase is substantially free from polygalacturonase, pectin lyase and other pectin depolymerase activities.

The pectin esterase of the present invention can be any pectin esterase from plants, bacteria or fungi, suitable for the degradation of apple pectin. Preferably, the pectin esterase is from fungal origin. More preferably, the pectin esterase is obtained from Aspergilli, especially preferred is the use of *Aspergillus niger*.

The present invention further discloses the enzymatic demethylation without depolymerization of apple pectin by a pectin esterase E.C.3.1.1.11. Preferably, the pectin esterase is applied during the apple pulp maceration step. Addition of this enzyme to the apple pulp gives an increased juice yield and an increased pressability with a concomitant increase in pressing rate.

In another aspect the present invention describes how the use of purified pectin esterase results in a larger amount of pectin remaining in the pomace. Furthermore, the use of purified pectin esterase reduces unwanted side-reactions (i.e. browning).

In still another aspect of the invention the valuable characteristics of the pectin obtained from the pomace after treatment with purified pectin esterase are disclosed.

BRIEF DESCRIPTION OF THE FIGURES

For all figures: R.PRESS is RAPIDASE RRESS; R.C80L is RAPIDASE C80L; PE is Pectin esterase; $Ca^{2+}$ is supplied in the form of $CaCl_2$

DETAILED DESCRIPTION OF THE INVENTION

In one aspect the present invention discloses a process for the production of juices and pectin-containing pomace from fruits and vegetables which comprises the use of a substantially pure pectin esterase (E.C. 3.1.1.11). The purified pectin esterase is substantially free from polygalacturonase, pectin lyase and other pectin depolymerase activities.

The use of the pectin esterase of the present invention gives rise to the enzymatic demethylation without depolymerization of pectin. The pectin may be from different origins. Preferably, apple pectin is used. The pectin esterase can be applied during several stages of the juice preparation process. Preferably, the pectin esterase is applied during the apple pulp maceration step.

Purified pectin esterase is characterized in that the amount of depolymerase activity contained in the enzyme preparation as determined by the combined action of pectin lyase and polygalacturonase is lower than 1 endo PG unit and lower than 20 exo PG units and lower than 0.4 PL units per 100 PE units, preferably lower than 0.1 endo PG units and lower than 2 exo PG units and lower than 0.04 PL units per 100 PE units.

The pectin esterase can be any pectin esterase from plants, bacteria or fungi, suitable for the degradation of pectins. The invention is exemplified using apple pectin. The pectin esterase suitable for use according to the present invention is stable in apple pulp or juice medium and retains its activity during the apple juice processing (pH 2.5–6.0, temperature 10°–68° C., organic acids, tannins). Due to the favourable enzymatic characteristics preferably fungal pectin esterases are used. Preferably, the pectin esterase is obtained from Aspergilli, more preferably from *Aspergillus niger*.

The crude pectin esterase coming from a culture medium can be purified in a number of ways. Preferably, the purification results in a product that is substantially free from polygalacturonase (PG) and pectin lyase (PL) activities. The crude enzyme may be purified for example by liquid chromatography (ion exchange, gel filtration, affinity) (Ishii et al, 1980. Deutsches Patentamt Auslegeschrift 2843351/C07G7/028) or by selective inhibition of the pectin depolymerases (pH shock, heat shock, chemical inhibitors, chemical or organic solvents extraction) (Smythe C. et al, 1952 U.S. Pat. No. 2,599,531). Another source for obtaining purified pectin esterase as defined for the present application is pectin esterase obtained by recombinant DNA technology. An example is the expression cloning of the *Aspergillus niger* pectin esterase for which the cDNA sequence has been determined (Khanh et al. Nucl. Acids Res. 18 4262 (1990)). As expression host *Aspergillus niger* could be used. However, in view of the possible contamination of the pectin esterase with polygalacturonase, pectin lyase and other pectin depolymerases it may be preferable to use a heterologous host organism for producing the pectin esterase. Suitable host organisms include bacteria and fungi. Preferred species would be Bacilli, Escherichia, Saccharomyces, Kluyveromyces and Aspergilli.

The purified pectin esterase can be used in the maceration of apple pulp obtained from both fresh apples and stored apples. Fresh apples are defined as apples which are treated from 1 to 3 months after the crop harvesting. Stored apples are defined as the fruits which have been stored in a cold room and/or under controlled atmospheric conditions and which are treated up until 6 months after crop harvesting.

Different apple varieties from different countries are treated directly or after a storage at 4° C. for several months. The choice of apples is mainly dependent on availability and is not critical. In the examples in support of the present invention the following apple varieties were used Granny Smith, Golden Delicious, Red Delicious and Akane from Europe, Ozargold and Primrouge from France and Granny Smith, Golden Delicious, Red Delicious and Braeburn from South America (Chile) and New Zealand. The South American and New Zealand apples have been harvested in March and stored at 4° C. Subsequent processing was between June and August. The experiments have been performed with both fresh and stored apples as described. The experiments have further been performed at lab, pilot and industrial scale as described.

After the fruit grinding, the purified pectin esterase is added in various amounts. Under the processing conditions the enzyme is reasonably stable. Therefore, the addition of a low amount of PE and the use of this low amount of enzyme during a longer period usually gives the same result as the addition of a higher amount of PE and a shorter working time. The amount of PE added (X Units) during the maceration can therefore best be given in relation with the working time (Y Time in hours). A workable range is as follows:

$$20,000 < X \text{ (PE Units)} * Y \text{ (hours)} < 500,000 \text{ per ton apples.}$$

With a maceration time of one hour this amounts to between 20,000 and 500,000 PE Units per ton of apples.

Purified pectin esterase can be used with or without additional calcium in the form of calcium chloride for the apple pulp maceration, depending on the maturity of the apples. The amount of calcium used is between 0 and 500 g calcium ions per ton of apples. Generally, lower amounts of calcium are used when apples are used earlier after harvesting. The definition of PE units is given in the Experimental section.

During the pressing step with hydraulic presses, the applied pressures and the juice weight have been recorded, subsequently the juice yield has been calculated using the juice density.

The use of a purified pectin esterase, either with or without addition of calcium, gives rise to the following improvements compared with juice production without enzyme addition:

increase of the free run juice volume before pressing with both fresh and stored apples, improvement of the pulp pressability due to calcium (exogenous or endogenous) binding with the demethylated pectin, shorter pressing time and thus a greater throughput, decrease of the water retention power of the pulp, increase of the total juice yield, increase of the filtration/ultra-filtration rate and increase of the concentratability of the juice, the amount of pectin extracted from treated pomace is the same as that extracted from pomace obtained without any enzymatic treatment, the composition of the pectin which is extracted from the pomace gives rise to similar gelifying characteristics as that extracted from pomace obtained without any enzymatic treatment.

In comparison with the use of classical pectinases, the use of a purified pectin esterase before pressing accounts for:

decrease of the oligogalacturonides content of the juice, avoiding partially the non-enzymatic browning of the juice which is less oxidizable and more stable during storage. The juice after enzymatic depectinization is less coloured and more limpid, decrease of the pectin content in the juice after pressing, the protopectin remains intact within the pomace and it is possible to sell it to pectin manufactures, mainly just after harvesting, when the apple pomace still has a high protopectin content.

Following the use of a purified pectin esterase it can be concluded that with a purified pectin esterase it becomes economically more attractive to prepare juices from fruits and vegetables. The juice yield and the pulp pressability are increased. The press capacity is increased thus it becomes possible to process a higher tonage of apples in a shorter time, providing moreover pomaces which still contain intact protopectin. Furthermore, the amount of side-reactions is lowered leading to a product which shows less browning.

Several aspects of the use of purified pectin esterase are illustrated in the examples. The examples only serve to illustrate the invention and are not meant to limit the scope in any way.

EXPERMINENTAL

Assay of pectin esterase activity

One PE unit is defined as the amount of enzyme which hydrolizes one micro-equivalent carboxymethyl in one minute under reaction conditions at 30° C. and pH=4.5. The substrate is Apple pectin Ruban Brun 0.5% with a methylation degree of over 70% in water.

One PE Unit=0.98 PE International Unit. Reaction conditions for the assay described here and below are standard for these assays. In general they are solutions of the indicated substrate buffered to the desired pH.

Assay of pectin lyase (PL) activity

One PL Unit is defined as the amount of enzyme producing one micromole of unsaturated $\triangle 4,5$ uronic product in one minute. The molar specific absorption of the product is $5.55 \times 10^3$. The reaction is performed at 45° C., pH 5.5 and the substrate is surmethylated pectin (1% w/v). The optical density, measured at 235 nm, is read after a reaction time of 10 minutes.

Assay of endo-Polygalacturonase (endo PG) activity

One endo PG Unit is defined as the amount of enzyme in 1 ml of enzymatic solution which decreases the substrate viscosity with a rate having an appearant rate constant of 0.0053 per minute under the reaction conditions at 45° C. and pH=4.5. The substrate is sodium polygalacturonate 0.5%.

Assay of exo-Polygalacturonase (exo PG) activity

One exo PG Unit is defined as the quantity of enzyme which catalyzes the hydrolysis of the α-1,4 bond in polygalacturonate forming one micromole of galacturonic acid in one minute at 30° C. at pH 4.5 (Schaeffer and Somogyi J. Biol. Chem. (1952) 195 p.19).

Turbidity

The juice turbidity is measured by nephelometry and expressed in NTU (Nephelometric Turbidity Units).

Colour

The juice absorbance is measured by spectrophotometry at optical densities of 420 and 520 nm.

Drying of the pomace

The desired amount of about 150 g of wet pomace is put in a beaker. 900 ml of distilled water is added and the mixture is left to stand for 15 minutes. Filtration is subsequently performed under vacuum on Supra 2600. After 1 night at 60° C. under ventilation the dry pomace is grinded to a powder.

Dry matter content of apple pomace

A weighted amount of pomace, of about 4 g, is put under infra-red light at 105° C. during 15 min. The weight of the residual dry matter is determined and expressed as percentage of the initial weight.

Chemical extraction of the apple pectin from the pomace

Weigh 200 g of apple pomace and add 900 ml of distilled water.

Leave the mixture 15 minutes for sugars dissolution in water.

Filtration under vacuum on carton Supra 2600.

Weigh the pomace after filtration.

Put the pomace at 60° C. for 1 night under ventilation.

Weigh the pomace.

Grind the pomace.

Put 5 g at 105° C. for 4 hours for the dry matter content calculation.

Put 10 g in a flask and add 190 ml of distilled water.

Heat under stirring until 100° C.

Add carefully 1.75 ml 2N $H_2SO_4$, cover the flask and keep it at 90° C. for 2.5 h in an oil bath.

Cooling and filtration through a nylon sheet.

Rince with water.

Precipitation with methanol, wash the alcohol insoluble substance (AIS) with 1.5 liter methanol.

Take the AIS and put it at 60° C. for 1 night under ventilation.

Weigh the residual material.

The percentage AIS is defined as follows:

$$\% AIS = \frac{\text{dry AIS weight} \times 100}{\text{wet weight} \times \text{dry matter content}}$$

The AIS content is a measure for the pectin content in the pomace. The AIS percentage is the measure used in price setting of the pomace.

Determination of esterification degree (E.D.) of pectin

Weigh 400 g of washed pectin in a 250 ml beaker,

Add 100 ml distilled, boiled water cooled to 50°–60° C.,

Cover the beaker and stir until the pectin is completely dissolved,

Add 4 drops of phenol phtalein,

Titrate with 0.1N NaOH until a pink colour appears ($V_1$ ml)

Add 20 ml 0.5N NaOH (pink colour),

Keep for 15 min. at room temperature in a sealed flask,

Neutralize with 0.5N HCl (no colour), 20 ml

Add 0.1N NaOH to get back a pink colour ($V_2$ ml),

As a blank use 100 ml distilled water ($\beta_1$ ml)

The esterification degree can now be found as follows:

$$\% E.D. = \frac{(V_2 - \beta_1) \times 100}{V_t} \quad \text{wherein } V_t = V_1 + (V_2 - \beta_1)$$

Determination of the molecular weight of pectin

Weigh about 90 g. of a 1% sodium hexa meta phosphate (MHP) solution (pH 4.5) in a 250 ml beaker, Heat the solution to 40°–45° C.

Add 100 mg pectin,

Stir until the pectin is completely dissolved,

Cool and add MHP until 100 g in total has been added,

Filter through 0.45 micrometer membrane (Swinnex-25),

Measure the viscosity with Oswald tube at 25° C.,

The molecular weight (M.W.) can be calculated using the following formula:

$$M.W. = 1{,}277 \times 10^6 (ur^{1/6} - 1)$$

$$ur = \frac{t_o - k/t_o}{t_h - k/t_h}$$

wherein:

$t_o$: time in s. between 2 marks on the tube for MHP+pectin solution.

$t_h$: time in s. for the MHP solution.

$$k = \frac{Q \times tv^2}{Q + (0.226 \times L \times tv)}$$

wherein

Q: volume between 2 marks on the tube (3.58 ml)

tv: time between 2 marks on the tube (94"15)

L: length between 2 marks on the tube (4.2 cm) here k=343.571

Pectin assay

The MHDP (metahydroxydiphenol) method has been used (Ahmed A. and Labavitch, J., 1977. J. Food Biochem. 1).

Apple varieties

Different apple varieties have been used from Europe and South America and New Zealand.

Enzyme addition

After grinding, the purified pectin esterase was added to the pulp in the range of 20,000< X (Units) * Y (hours) <500,000 PE Units per ton of apples with calcium from 0 to 500 g $Ca^{++}$ per ton of apples, supplied in the form of anhydrous $CaCl_2$. The pectin esterase alone or with calcium was mixed with the apple pulp.

Enzymatic maceration

The enzymatic maceration was carried out from 10 to 75 minutes from 15° to 25° C.

EXAMPLES

Example 1

A mixture of the apple varieties Golden Delicious, Granny Smith and Red Delicious (1:1:1) all from Europe was grinded and enzyme was added before pressing.

Figure 1:
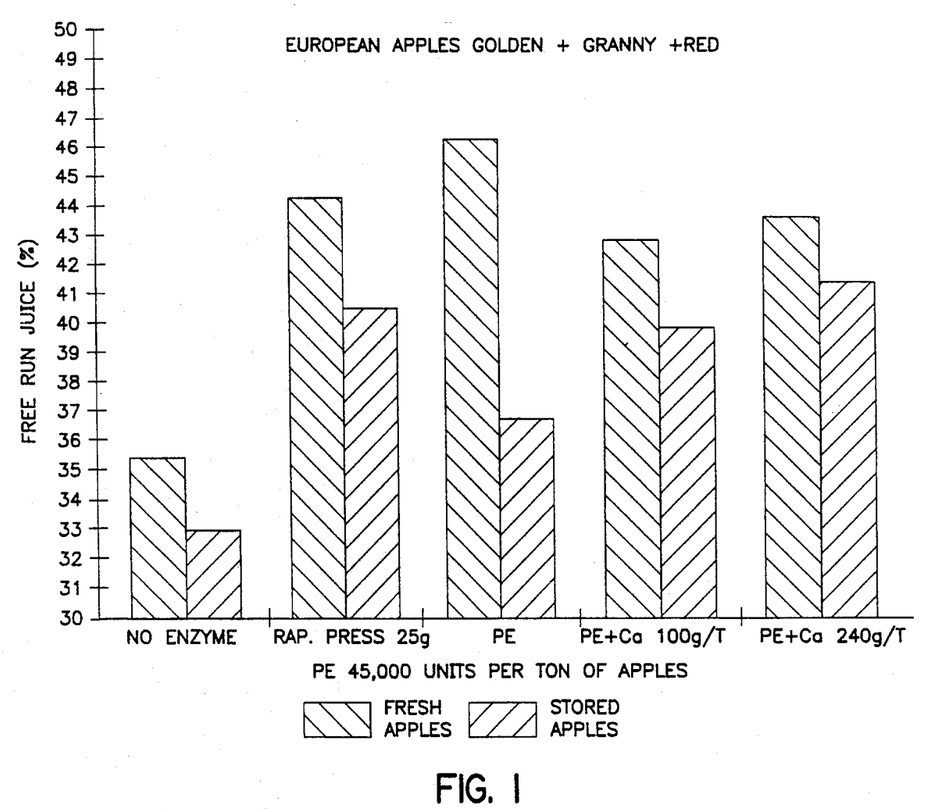
FIG. 1 shows the free run juice in % obtained before pressing from fresh and stored apples, after the pulp maceration with no enzyme, R.PRESS and a fixed PE activity and increasing amounts of calcium.

Enzymes used were: Rapidase Press™ at 25 g per ton of apple pulp, purified pectin esterase (PE) at 45,000 PE Units without or with calcium ions at 100 and 240 g per ton of apple pulp. After one hour at 20° C. the treated pulp was pressed using an hydraulic press. The free run juice was measured (FIG. 1).

Purified PE gives the highest free run juice volume with fresh apples, this gives rise to a higher press capacity. The use of purified PE gives a higher amount of free run juice volume with stored apples than that obtained without addition of enzyme.

Calcium ions have a more important role for the increase of the free run juice volume of stored apples than fresh apples, and this increase is related to the calcium dose.

Figure 2:
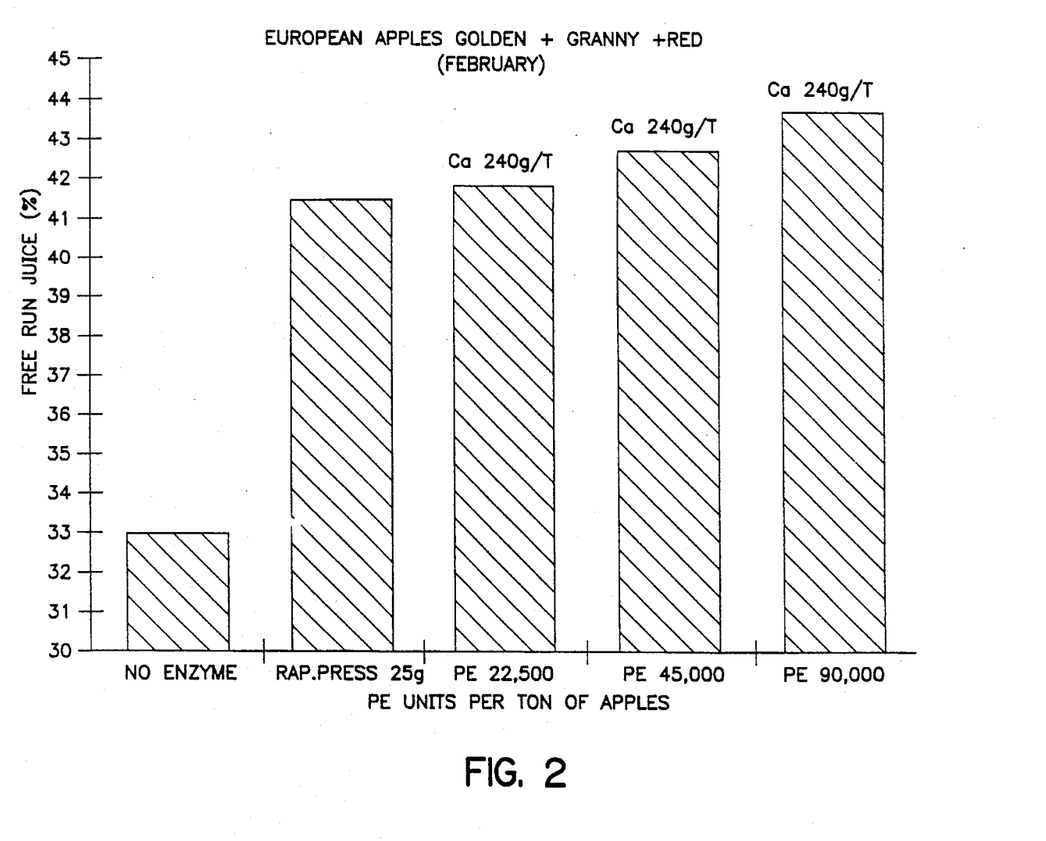
FIG. 2 shows the free run juice in % obtained before pressing from stored apples when using increasing PE activities and a fixed amount of calcium.

FIG. 2 shows the dependence of free run juice volumes on the purified PE dosage. With a constant amount of calcium ions at 240 g per ton, with stored apples, the use of the purified PE provides free run juice volume similar to the volume obtained with Rapidase Press™ at 25 g per ton and this amount is always better than the control without pressing enzyme.

Table 1 shows the lower colour and the lower turbidity of juices which come from pulp macerated with PE than without enzyme addition. The difference is even more pronounced when PE is used in combination with calcium.

TABLE 1

|  | O.D 420nm | 520nm | Turbidity NTU |
|---|---|---|---|
| no enzyme | 0.519 | 0.090 | 2.70 |
| PE 43,500 U/T | 0.437 | 0.078 | 2.70 |
| PE 43,500 U/T + Ca 200g/T | 0.293 | 0.050 | 2.70 |
| PE 130,000 U/T | 0.343 | 0.056 | 1.74 |
| PE 130,000 U/T + Ca 200g/T | 0.260 | 0.041 | 1.43 |

Figure 3:
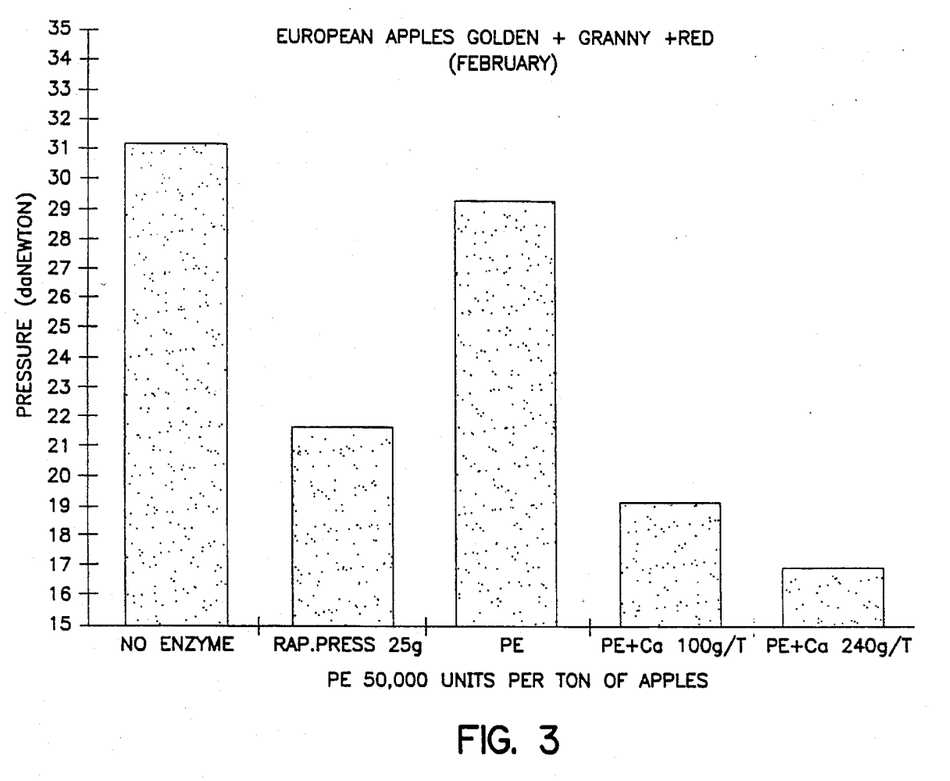
FIG. 3 shows the pressure which it is necessary to apply to get a constant juice weight after the pulp maceration of stored apples with no enzyme, R.PRESS and a fixed PE activity and increasing amounts of calcium.

FIG. 3 gives the pressure applied to the apple pulp to obtain the same juice production (400 g), using the different enzymes. With the stored apples, the pressure required on the apple pulp is lowest when using purified PE at 50,000 PE Units per ton with calcium ions at 240 g per ton of apple pulp. The decrease of pressure is related to the pulp pressability and proportional to the calcium ion content for a constant PE activity per pressing trial.

Figure 4:
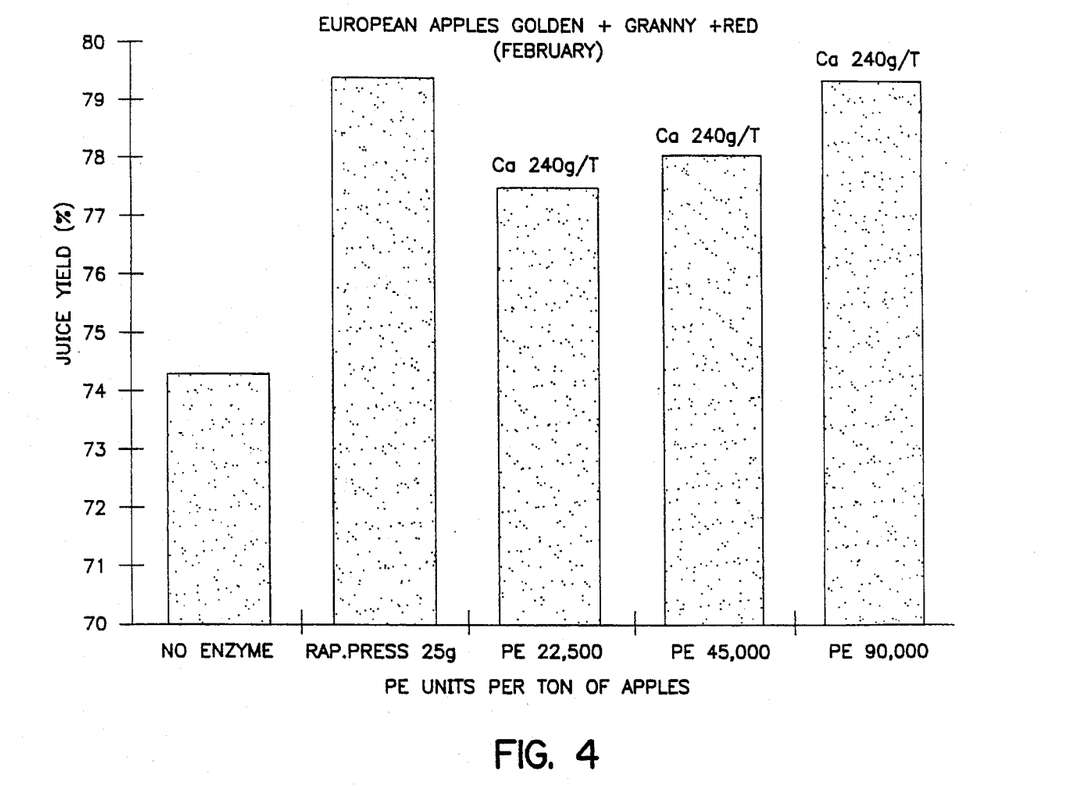
FIG. 4 shows the pressing juice yield in % obtained from stored apples after the pulp maceration with no enzyme, R.PRESS and increasing PE activities and a fixed amount of calcium.

FIG. 4 gives the final apple juice yield in percent obtained without enzyme, with Rapidase Press™ and with different PE activities, added together with a fixed amount of calcium ions of 240 g per ton. The juice yield is very high with Rapidase Press™ and still higher than the control with the purified PE with calcium.

Example 2

Apple varieties were Golden Delicious, Granny Smith, Red Delicious and Breaburn (equal amounts) from South America (Chile) and New Zealand. They have been harvested in March and stored at 4° C. to be processed between June and August. We call fresh apples the fruits which have been treated from 1 to 3 months after the crop and stored apples the fruits which have been stored at 4° C. and treated until 6 months after the crop.

The enzymatic preparation is mixed to the grinded apple pulp (12 kg per trial). The enzymatic maceration takes place in a tank at about 25° C. during 1 hour. The treated pulp is loaded into a Bucher Press HP14 which press with a pressure of about 10 bars. The juice is flowing out by an opening at the bottom of the press. The pressing time and the juice weight are recorded. The juice density is measured and the amount of sugar extracted calculated with the Goldiner & Klemann table. The final juice weight is corrected to a degree of 13.32% dry matter content (density=1.052 at 20° C.). The juice yield is related to the starting pulp weight (12 kg).

Figure 5:
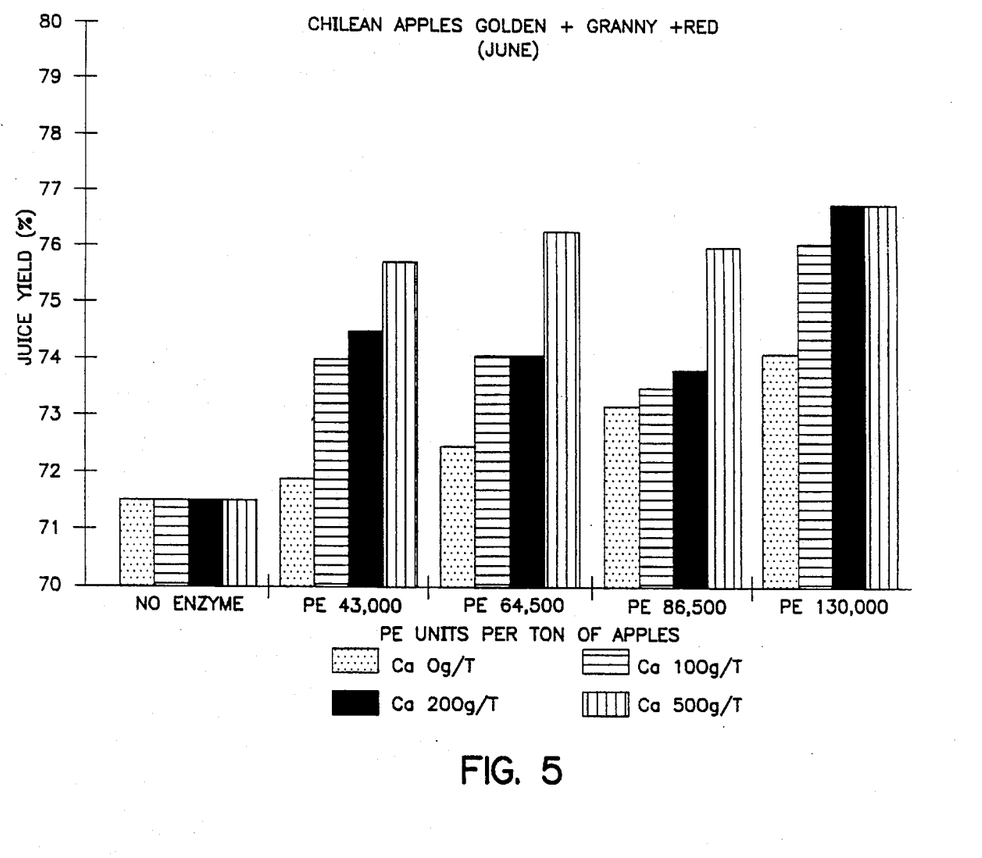
FIG. 5 shows the pressing juice yield in % obtained from fresh apples after the pulp maceration with increasing PE activities and increasing amounts of calcium.

The purified pectin esterase PE has been used from 43,500 to 130,000 PE Units without or with calcium from 100 to 500 g per ton of apple pulp. The apple juice yield is given as a percentage of total juice (FIG. 5). The yield is always higher with fresh apples after the use of the purified PE than without the addition of enzyme. However, the apples that are 3 months old give a higher juice yield after the addition of calcium ions to the purified PE. The difference in yield can amount to 5%.

Table 2 shows a lower content of pectin in the juice after treatment of the pulp with PE than with Rapidase Press™ and even with no enzyme.

TABLE 2

|  | Juice Pectin content g/L |
|---|---|
| no enzyme | 1.01 |
| R.PRESS 25g/T | 1.85 |
| PE 45,000 U/T | 0.97 |
| PE 45,000 U/T + Ca 240g/T | 0.85 |

Figure 6:
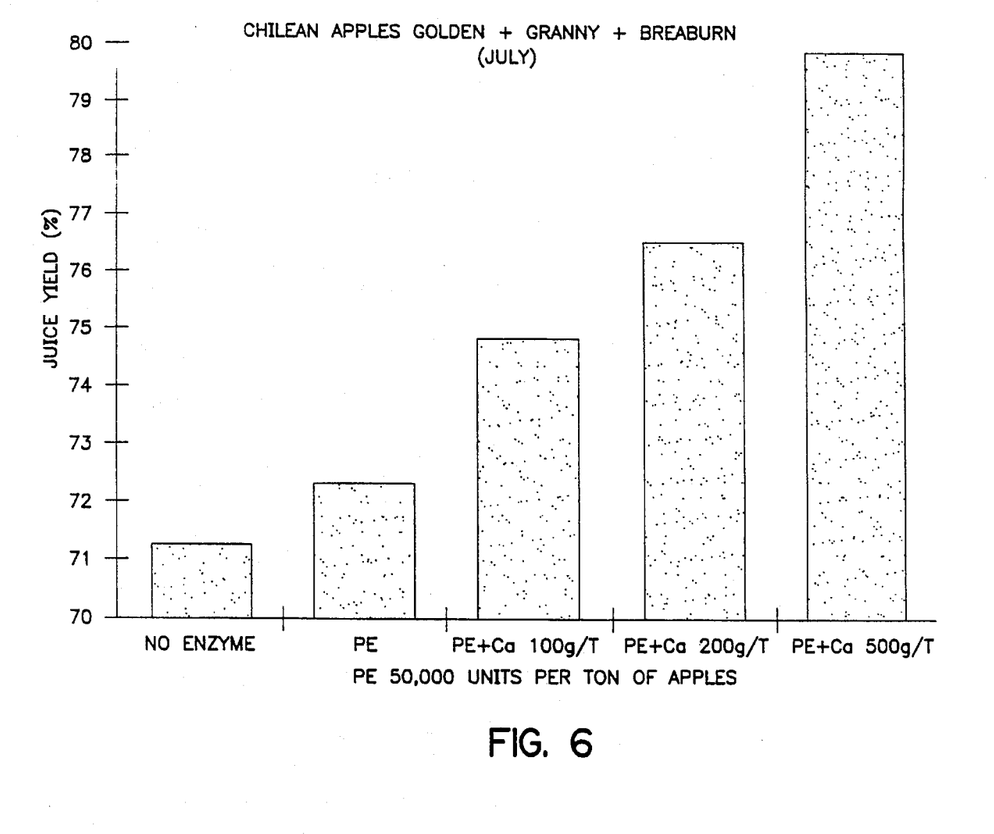
FIG. 6 shows the pressing juice yield in % obtained from stored apples after the pulp maceration with a fixed PE activity and increasing amounts of calcium.

FIG. 6 shows the effect of the calcium ions added to the purified PE on the apple juice yield. For a constant PE activity of 50,000 PE Units per ton of apple pulp, the juice yield is increasing with increasing calcium ions dosage between 0 and 500 g per ton of apple pulp. The use of the purified PE alone gives a higher apple juice yield than the control without enzyme.

Example 3

Apple varieties were Golden Delicious and Akane from France. They have been harvested in September and immediately processed at lab scale. The enzymatic preparation was mixed with the grinded apple pulp (750 g per trial). The enzymatic maceration takes place in a tank at 20° C. during 60 minutes. The treated pulp was loaded into a cloth bag and put into the press truck. The pulp was pressed with a hydraulic lab press (Adamel Lhomargy) with a pressure between 6 and 1,000 decaNewton. The juice was flowing out through an opening at the bottom of the press. The applied pressure and the juice weight were recorded. The juice density was measured and the amount of sugar extract calculated with the Goldiner & Klemann table. The final juice weight was corrected to a degree of 13.32% dry matter content (density=1.052 at 20° C.). The juice yield was related to the starting pulp weight (750 g).

Figure 7:
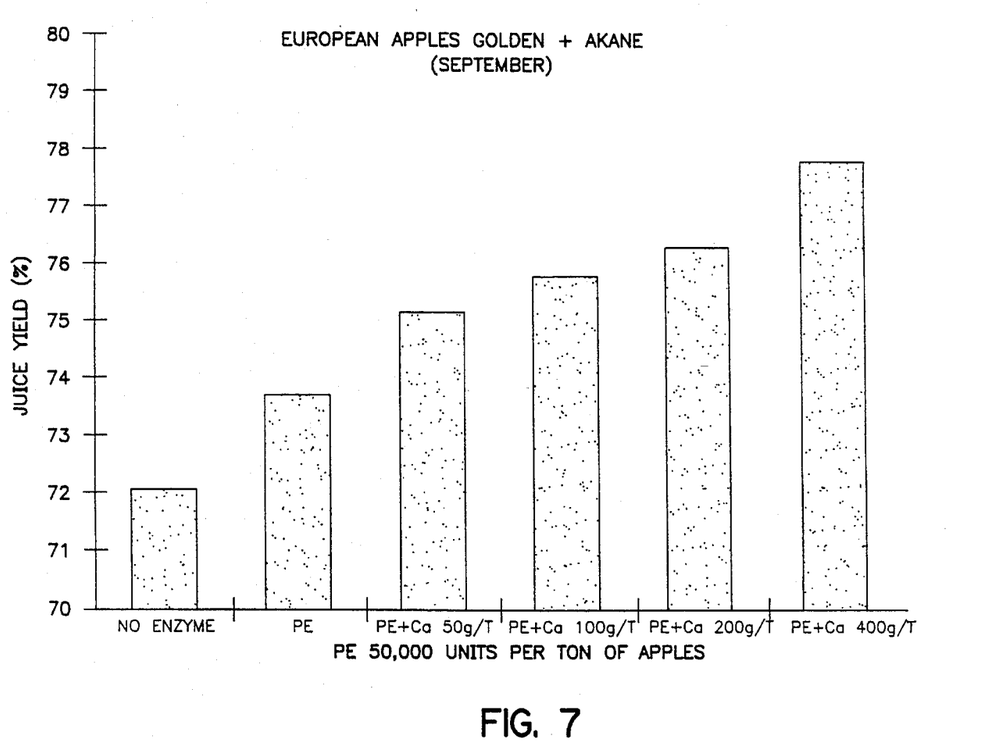
FIG. 7 shows the pressing juice yield in % obtained from fresh apples after the pulp maceration with a fixed PE activity and increasing amounts of calcium.

FIG. 7 shows the effect of calcium ions added to the purified PE on the apple juice yield. For a fixed PE activity of 50,000 PE Units per ton of apple pulp, the juice yield is increasing proportionally with the calcium ions dosage, between 0 and 400 g per ton of apple pulp. The use of purified PE alone already gives rise to a higher apple juice yield than the control without enzyme.

Figure 8:
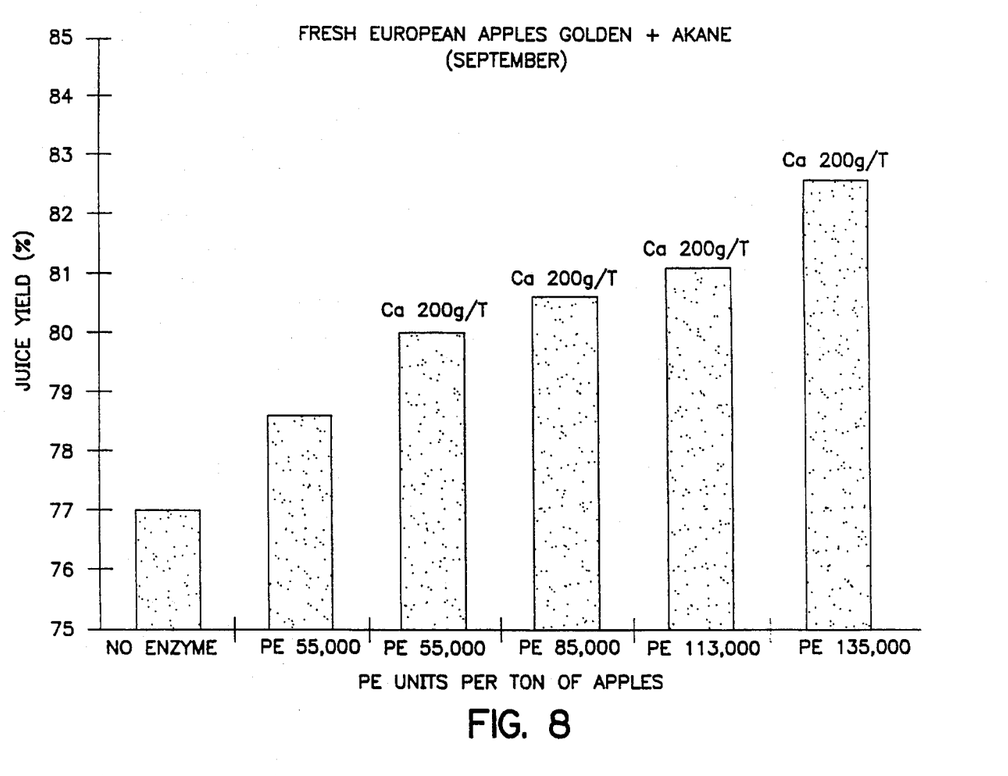
FIG. 8 shows the pressing juice yield in % obtained from fresh apples after the pulp maceration with increasing PE activities and a fixed amount of calcium.

FIG. 8 shows the effect of the purified PE activity on the juice yield of fresh apples. As can be seen juice yield is increasing from 79 to 84% through the addition of purified PE.

Example 4

Apple varieties were Ozargold/Primrouge from France. They have been harvested in August and immediately processed at lab scale. The enzymatic preparation was mixed with the grinded apple pulp (750 g per trial). The enzymatic maceration takes place in a tank at 20° C. during 60 minutes. The treated pulp was loaded into a cloth bag and put into the press truck. The pulp was pressed with a hydraulic lab press (Adamel Lhomargy) with a pressure between 6 and 1,000 decaNewton. The juice was flowing out through an opening at the bottom of the press. The applied pressure and the juice weight were recorded. The juice density was measured and the amount of sugar extract calculated with the Goldiner & Klemann table. The final juice weight was corrected to a degree of 11.32% dry matter content (density=1.052 at 20° C.). The juice yield was related to the starting pulp weight (750 g).

Figure 9:
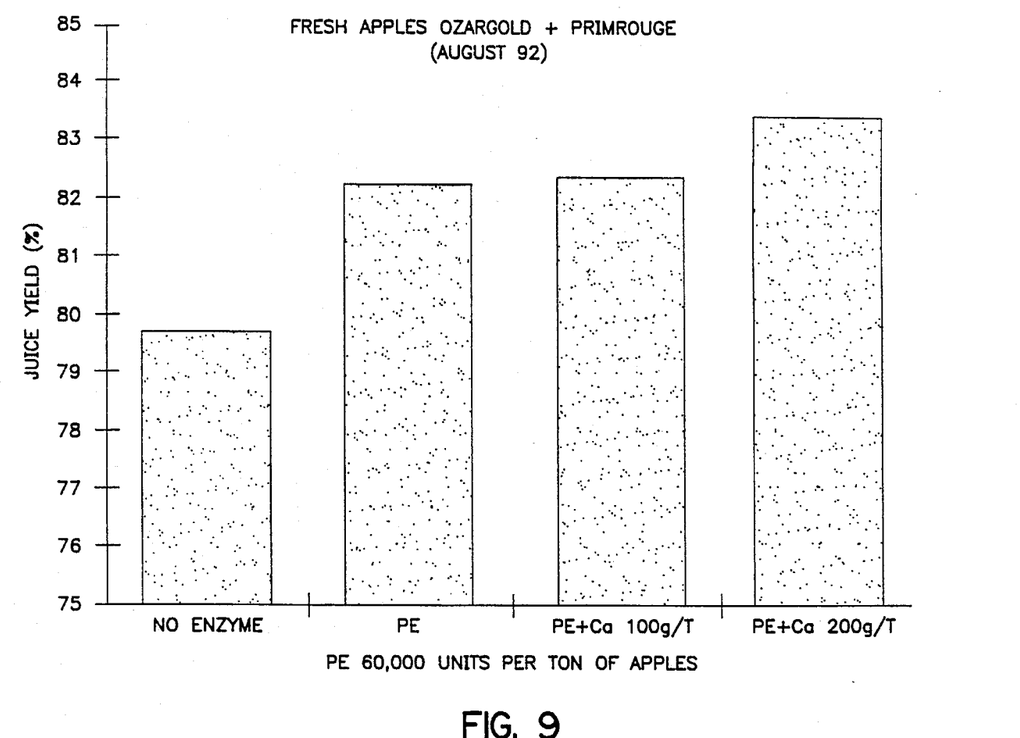
FIG. 9 shows the pressing juice yield in % obtained from fresh apples after pulp maceration with a fixed PE activity and increasing amounts of calcium.

FIG. 9 shows the effect of the purified PE on the apple juice yield. Addition of 60,000 PE units per ton of apple pulp gave rise to a 2.6% increase in apple juice yield. An addition of 60,000 PE units plus 100–200 g calcium ions per ton of apple pulp allows for an increase in juice yield of 3–3.5%. The pressure applied to obtain an equal amount of juice is lower when PE is added to the pulp. Both pulp pressability and press productivity increase.

Figure 10:
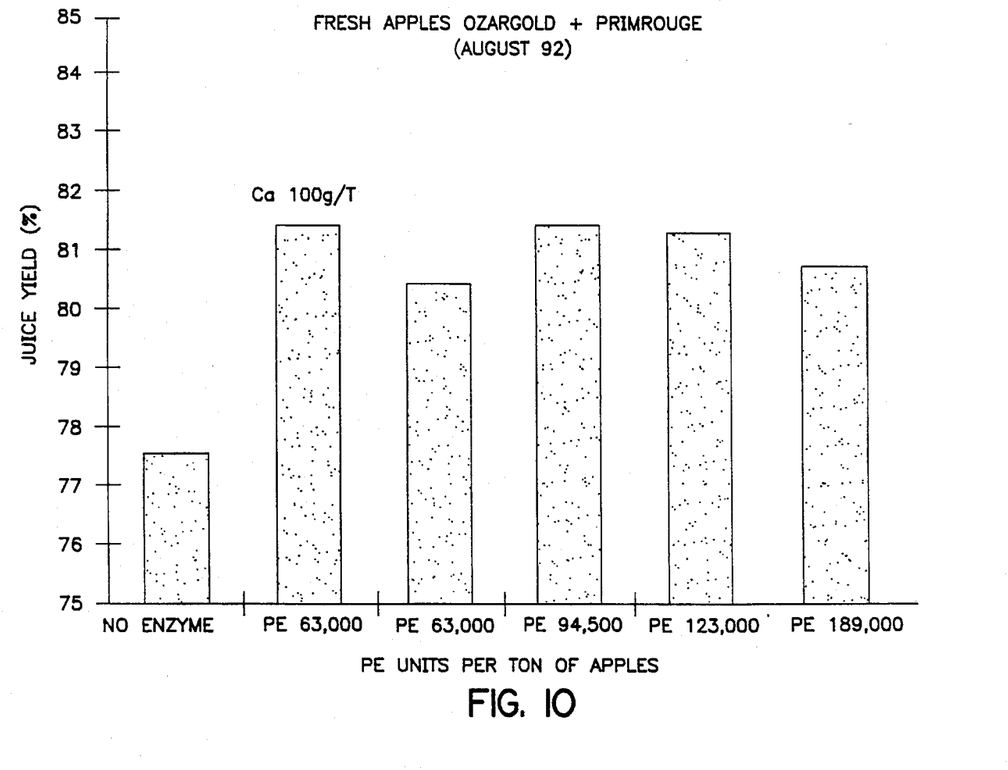
FIG. 10 shows the pressing juice yield in % obtained from fresh apples after pulp maceration with increasing PE activities.

FIG. 10 shows that there is no absolute need to add calcium to the PE to treat apples just after the crop since 94,500 PE units gives almost the same juice yield as 63,000 PE units plus calcium ions at 100 g per ton of apples.

TABLE 3

|  |  | Juice yield | Pomace Pectin % | E.D.% | M.W. |
|---|---|---|---|---|---|
| Control |  | 77.55 | 23.8 | 74.19 | 76.241 |
| PE | 63,000 U/T | 80.33 | 23.0 | 71.64 | 70.510 |
| PE | 63,000 U/T + Ca 200 g/T | 81.42 | 23.0 | 66.87 | 70.989 |
| PE | 94,500 U/T | 81.36 | 23.1 | 66.94 | 71.427 |
| PE | 126,000 U/T | 81.35 | 22.8 | 67.11 | 64.828 |
| PE | 189,000 U/T | 80.72 | 22.9 | 68.53 | 67.107 |

From Table 3 the following conclusions can be drawn:

the addition of a pure PE to the apple pulp increases the juice yield in comparison with no enzyme with fresh apples, an addition of 60–65,000 PE units/ton improves the juice yield by about 2.5–3%.

Addition of calcium ions in addition to PE increase the yield by about 1–2.5%.

The addition of 94,500 PE U/ton gives the same result as 63,000 U/ton plus 200 g/t calcium.

The pectin content of the pomace after treatment with PE is at least 95% of the initial value. The minimum pectin contend of the pomace required by pectin producers is 14%. With figures (Table 3) higher than 20%, the pomace belongs to the pectin content group with the highest value.

The pectin E.D. and M.W. are not very different from the control (max. −5% E.D. and max. 7% M.W.).

The PE does not degrade the unsoluble protopectin of the pomace (quantity - E.D. - M.W.), but allows higher juice yields for the producer.

Example 5

Apple varieties were Golden Delicious, Jonathan, Gloster and Starking. They have been harvested in September and processed within 1 week (juice pH=3.4). The enzymatic preparation was mixed with the grinded apple pulp using a dosis pump. The enzymatic maceration took place in a tank (12 tons) at 17° C. during 1 hour. The treated pulp was loaded into a Bucher Press. The juice weight is recordered. The juice brix was always 12% (brix meter). The purified PE was used in amounts varying from 42,000 to 126,000 PE units per ton with 0 or 50 g calcium/ton.

TABLE 4

|  |  | Juice yield % | Pomace dry matter % |
|---|---|---|---|
| Control |  | 78.7 | 24.2 |
| PE | 42,000 U/T | 78.8 | 24.2 |
| PE | 84,000 U/T | 79.6 | 24.3 |
| PE | 126,000 U/T | 79.7 | 26.9 |
| PE | 84,000 U/T + Ca 50 g/T | 81.6 | 26.0 |
| R.Press | 25 g/T | 83.9 | 26.3 |

TABLE 5

|  | Juice Colour | | Ultra-filtration |
|---|---|---|---|
|  | O.D. 420 | 520 nm | flux rate |
| Control | 0.57 | 0.13 | 60 l/m2/hour |
| PE 84,000 U/T | 0.23 | 0.06 | 80 |

The juice yield is improved by addition of PE.

The dry matter content of the pomace increases in relation with the PE dosage.

The colour of the juice is lower after PE treatment.

The ultra-filtration flux rate is improved by ⅓.

We claim:

1. A process for the production of juices and pectin-containing pomace from a fruit or a vegetable which process comprises contacting the pulp of said fruit or vegetable in the presence of calcium ions with a pectin-attacking enzyme composition consisting essentially of pectin esterase under conditions wherein said pectin esterase effects enzymatic demethylation without depolymerization of pectin; and separating the resulting juices from the resulting pectin-containing pomace.

2. The process of claim 1 wherein the amount of depolymerase activity is less than 1 endo PG unit and less than 20 exo PG units and less than 0.4 PL units per 100 PE.

3. The process of claim 2 wherein the amount of depolymerase activity is less than 0.1 endo PG units and less than 2 exo PG units and less than 0.04 PL units per 100 PE units.

4. The process of claim 1 wherein the pectin esterase is obtainable from bacteria or fungi.

5. The process of claim 4 wherein the pectin esterase is obtainable from Aspergillus.

6. The process of claim 5 wherein the pectin esterase is obtainable from *Aspergillus niger*.

7. The process of claim 1 wherein said fruit is apple.

8. The process of claim 1 wherein said contacting further includes contacting said fruit pulp or vegetable pulp with exogenous calcium ions.

9. The process of claim 8 wherein said calcium ions are present in an amount less than 500 grams per ton of apple pulp.

10. The process of claim 1 wherein said contacting employs 20,000–500,000 PE units per ton of apple pulp per hour of contacting time.

11. A method to prepare pectin which method comprises:

drying the pectin-containing pomace obtained by the process of claim 1;

extracting the sugars from said dried pomace to result in a pectin-containing residue;

extracting the pectin from said pectin-containing residue in an aqueous solution; and precipitating the pectin from the solution.

* * * * *